United States Patent
Downey

(10) Patent No.: US 8,176,978 B2
(45) Date of Patent: May 15, 2012

(54) METHOD FOR OPTIMIZING IN-SITU BIOCONVERSION OF CARBON-BEARING FORMATIONS

(75) Inventor: Robert A. Downey, Centennial, CO (US)

(73) Assignee: Ciris Energy, Inc., Centennial, CO (US)

( * ) Notice: Subject to any disclaimer, the term of this patent is extended or adjusted under 35 U.S.C. 154(b) by 143 days.

(21) Appl. No.: 12/459,416

(22) Filed: Jul. 1, 2009

(65) Prior Publication Data
US 2010/0000732 A1 Jan. 7, 2010

Related U.S. Application Data

(60) Provisional application No. 61/133,757, filed on Jul. 2, 2008.

(51) Int. Cl.
*E21B 43/22* (2006.01)
(52) U.S. Cl. ......... 166/246; 166/275; 166/279; 166/370
(58) Field of Classification Search .................. None
See application file for complete search history.

(56) References Cited

U.S. PATENT DOCUMENTS

| | | | |
|---|---|---|---|
| 1,606,015 A | 11/1926 | Blackwell | |
| 2,992,093 A | 7/1961 | Burdick | 71/24 |
| 3,076,291 A | 2/1963 | Gardner | 47/58 |
| 3,111,404 A | 11/1963 | Karcher et al. | 71/24 |
| 3,264,064 A | 8/1966 | Natta | 23/203 |
| 3,352,902 A | 11/1967 | Moschopedas | 260/507 |
| 3,398,186 A | 8/1968 | Schwartz | 260/515 |
| 3,418,100 A | 12/1968 | Cooley | 71/24 |
| 3,544,295 A | 12/1970 | Nakamigawa et al. | 71/1 |
| 3,574,649 A | 4/1971 | Fanti et al. | 117/106 |
| 3,607,211 A | 9/1971 | Cole et al. | 71/1 |
| 3,674,649 A | 7/1972 | Formisano et al. | 195/104 |
| 3,711,392 A | 1/1973 | Metzger | 204/180 |

(Continued)

FOREIGN PATENT DOCUMENTS

WO WO 87/06254 10/1987

(Continued)

OTHER PUBLICATIONS

Ahmed, et al., Advanced Reservoir Engineering, p. 3/226 Gulf Professional Publishing / Elsevier.

(Continued)

*Primary Examiner* — Zakiya W Bates
(74) *Attorney, Agent, or Firm* — Carella, Byrne, et al.; Elliot M. Olstein

(57) ABSTRACT

Processes relating to the production of methane, carbon dioxide, gaseous and liquid hydrocarbons, and other valuable products from subterranean carbon bearing formations, in-situ, are disclosed. In a preferred embodiment, such production utilizes indigenous and/or non-indigenous microbial consortia that are capable of converting a carbon bearing material such as shale or coal to desired products. In a particularly preferred embodiment there is provided a process for bioconverting a carbon-bearing subterranean formation, wherein the process comprises injecting fluid into a carbon bearing deposit with at least one injection well and removing injected fluid and product from the deposit through at least one production well, and controlling fluid pressure within at least a portion of the deposit by use of the injected fluid, the pressure being controlled such that the fluid pressure within at least a portion of the deposit exceeds the fluid pressure that normally exists in that portion.

27 Claims, 1 Drawing Sheet

U.S. PATENT DOCUMENTS

| | | | |
|---|---|---|---|
| 3,744,566 A | 7/1973 | Szabo et al. | 166/275 |
| 3,770,411 A | 11/1973 | Chambers et al. | 71/24 |
| 3,981,803 A | 9/1976 | Coulthard | 210/178 |
| 3,990,513 A | 11/1976 | Perch | 166/267 |
| 4,007,789 A | 2/1977 | Clampitt | 166/281 |
| 4,021,329 A | 5/1977 | Seitzer | 208/10 |
| 4,206,288 A | 6/1980 | Detz et al. | 435/267 |
| 4,257,869 A | 3/1981 | Dickert et al. | 208/8 |
| 4,259,084 A | 3/1981 | Liotta | 44/1 |
| 4,274,760 A | 6/1981 | Norman | 405/163 |
| 4,298,450 A | 11/1981 | Ross et al. | 208/8 |
| 4,298,621 A | 11/1981 | Samis et al. | 426/55 |
| 4,319,041 A | 3/1982 | Goff | 562/475 |
| 4,321,076 A | 3/1982 | Firth, Jr. | 71/24 |
| 4,366,073 A | 12/1982 | McLaughlin | 252/8.55 R |
| 4,394,136 A | 7/1983 | Grabis | 48/111 |
| 4,397,953 A | 8/1983 | Guazzone et al. | 435/243 |
| 4,400,195 A | 8/1983 | Rijkens | 71/10 |
| 4,436,818 A | 3/1984 | Widmer | 435/316 |
| 4,451,351 A | 5/1984 | Porter et al. | 208/10 |
| 4,501,445 A | 2/1985 | Gregoli | 299/2 |
| 4,541,914 A | 9/1985 | Hirokoh et al. | 208/10 |
| 4,613,434 A | 9/1986 | Maatta | 210/151 |
| 4,632,692 A | 12/1986 | Lebesgue et al. | 71/10 |
| 4,647,537 A | 3/1987 | Shigemitsu | 435/178 |
| 4,654,308 A | 3/1987 | Safi et al. | 435/310 |
| 4,659,670 A | 4/1987 | Stevens, Jr. et al. | 435/262 |
| 4,675,294 A | 6/1987 | Finck et al. | 435/167 |
| 4,728,418 A | 3/1988 | Shabtai et al. | 208/413 |
| 4,731,179 A | 3/1988 | De Baere | 210/251 |
| 4,735,706 A | 4/1988 | Ruether | 208/426 |
| 4,775,627 A | 10/1988 | Attia et al. | 435/262 |
| 4,787,456 A | 11/1988 | Jennings et al. | 166/281 |
| 4,798,801 A | 1/1989 | Hitzman | 435/313 |
| 4,845,034 A | 7/1989 | Menger et al. | 435/167 |
| 4,846,963 A | 7/1989 | Knudson et al. | 208/408 |
| 4,861,519 A | 8/1989 | Tusa et al. | 252/633 |
| 4,882,274 A | 11/1989 | Pyne, Jr. et al. | 435/68 |
| 4,914,024 A | 4/1990 | Strandberg et al. | 435/41 |
| 4,948,509 A | 8/1990 | Stack | 210/643 |
| 4,985,060 A | 1/1991 | Higa | 71/6 |
| 4,997,202 A | 3/1991 | Kitagawa et al. | 280/719 |
| 5,009,340 A | 4/1991 | Morane | 222/94 |
| 5,014,785 A | 5/1991 | Puri et al. | 166/263 |
| 5,026,416 A | 6/1991 | Alexander | 71/24 |
| 5,034,045 A | 7/1991 | Alexander | 71/24 |
| 5,091,315 A | 2/1992 | McCarty et al. | 435/287 |
| 5,120,430 A | 6/1992 | Morgan | 208/428 |
| 5,180,494 A | 1/1993 | Yamaguchi et al. | 210/603 |
| 5,182,199 A | 1/1993 | Hartley | 435/162 |
| 5,207,911 A | 5/1993 | Pellegrin et al. | 210/603 |
| 5,282,879 A | 2/1994 | Baccarani | 71/10 |
| 5,294,349 A | 3/1994 | Kramer et al. | 208/400 |
| 5,298,163 A | 3/1994 | Ehlinger | 210/603 |
| 5,363,913 A | 11/1994 | Jenneman et al. | 166/246 |
| 5,389,258 A | 2/1995 | Smis et al. | 210/603 |
| 5,424,195 A | 6/1995 | Volkwein | 435/34 |
| 5,447,208 A | 9/1995 | Lund et al. | 175/428 |
| 5,447,850 A | 9/1995 | McCann | 435/42 |
| 5,486,214 A | 1/1996 | Paszczynski et al. | 8/524 |
| 5,490,634 A | 2/1996 | Jain et al. | 241/1 |
| 5,523,234 A | 6/1996 | Fichet | 435/289 |
| 5,560,737 A | 10/1996 | Schuring et al. | 405/128 |
| 5,566,756 A | 10/1996 | Chaback et al. | 166/263 |
| 5,605,198 A | 2/1997 | Tibbitts et al. | 175/432 |
| 5,653,300 A | 8/1997 | Lund et al. | 175/428 |
| 5,670,345 A | 9/1997 | Srivastava et al. | 435/75 |
| 5,773,526 A | 6/1998 | Van Dijk et al. | 210/603 |
| 5,787,022 A | 7/1998 | Tibbitts et al. | 364/578 |
| 5,792,355 A | 8/1998 | Desjardins | 210/605 |
| 5,854,032 A | 12/1998 | Srivastava et al. | 435/75 |
| 5,950,747 A | 9/1999 | Tibbitts et al. | 175/432 |
| 5,967,250 A | 10/1999 | Lund et al. | 175/428 |
| 6,021,859 A | 2/2000 | Tibbitts et al. | 175/431 |
| 6,043,392 A | 3/2000 | Holtzapple et al. | 562/513 |
| 6,143,534 A | 11/2000 | Menger et al. | 435/167 |
| 6,145,608 A | 11/2000 | Lund et al. | 175/428 |
| 6,180,396 B1 | 1/2001 | Ono et al. | 435/289 |
| 6,262,313 B1 | 7/2001 | Holtzapple et al. | 568/397 |
| 6,338,390 B1 | 1/2002 | Tibbitts | 175/56 |
| 6,342,378 B1 | 1/2002 | Zhang et al. | 435/168 |
| 6,368,849 B1 | 4/2002 | Norddahl | 435/262 |
| 6,423,532 B1 | 7/2002 | Rindelaub | 435/262.5 |
| 6,440,307 B1 | 8/2002 | Philip et al. | 210/617 |
| 6,543,535 B2 | 4/2003 | Converse et al. | 166/246 |
| 6,555,350 B2 | 4/2003 | Ahring et al. | 435/162 |
| 6,679,326 B2 | 1/2004 | Zakiewicz | 166/272.5 |
| 6,773,596 B2 | 8/2004 | Penzes et al. | 210/605 |
| 6,814,141 B2 | 11/2004 | Huh et al. | 166/249 |
| 6,814,992 B2 | 11/2004 | Pazik et al. | 426/231 |
| 6,852,226 B2 | 2/2005 | Hiro et al. | 210/603 |
| 6,905,601 B2 | 6/2005 | De Baere et al. | 210/603 |
| 7,015,028 B2 | 3/2006 | Choate et al. | 435/262.5 |
| 7,045,063 B2 | 5/2006 | Zhang et al. | 210/603 |
| 7,225,085 B2 | 5/2007 | Zhang et al. | 702/45 |
| 7,316,921 B2 | 1/2008 | Choate et al. | 435/283.1 |
| 7,556,737 B2 | 7/2009 | Zhang | 210/603 |
| 2001/0045279 A1 | 11/2001 | Converse et al. | 166/246 |
| 2002/0017629 A1 | 2/2002 | Mosier et al. | 252/71 |
| 2003/0210956 A1* | 11/2003 | Tanaka et al. | 405/128.25 |
| 2004/0033557 A1 | 2/2004 | Scott et al. | 435/42 |
| 2004/0110645 A1 | 6/2004 | Campbell | 507/200 |
| 2004/0203134 A1 | 10/2004 | Pyntikov et al. | 435/252.1 |
| 2005/0118130 A1 | 6/2005 | Utz et al. | 424/70.13 |
| 2006/0131074 A1 | 6/2006 | Calhoun et al. | 175/50 |
| 2006/0223153 A1 | 10/2006 | Pfeiffer et al. | 435/166 |
| 2006/0223159 A1 | 10/2006 | Pfeiffer et al. | 435/252.1 |
| 2006/0223160 A1 | 10/2006 | Vanzin | 435/252.4 |
| 2006/0254765 A1 | 11/2006 | Pfeiffer et al. | 166/246 |
| 2007/0048848 A1 | 3/2007 | Sears | 435/134 |
| 2007/0078665 A1 | 4/2007 | Dodson et al. | 705/1 |
| 2007/0158264 A1 | 7/2007 | Zhang | 210/603 |
| 2007/0161077 A1 | 7/2007 | Pfeiffer et al. | 435/41 |
| 2007/0191303 A1 | 8/2007 | Dillon et al. | 514/54 |
| 2007/0243235 A1 | 10/2007 | David | 424/442 |
| 2007/0244227 A1 | 10/2007 | Eipper et al. | 523/400 |
| 2007/0251146 A1 | 11/2007 | Larter et al. | 48/127.5 |
| 2007/0261843 A1 | 11/2007 | Pfeiffer et al. | 166/246 |
| 2007/0295505 A1 | 12/2007 | Pfeiffer et al. | 166/263 |
| 2008/0051599 A1 | 2/2008 | Adami et al. | 560/129 |
| 2009/0193712 A1 | 8/2009 | Verkade et al. | 44/620 |
| 2010/0000732 A1 | 1/2010 | Downey | 166/268 |
| 2010/0032157 A1 | 2/2010 | Downey | 166/275 |
| 2010/0068772 A1 | 3/2010 | Downey | 435/134 |
| 2010/0081184 A1 | 4/2010 | Downey et al. | 435/167 |
| 2010/0139913 A1 | 6/2010 | Downey | 166/246 |

FOREIGN PATENT DOCUMENTS

| | | |
|---|---|---|
| WO | WO 2005/113784 A1 | 12/2005 |
| WO | WO 2005/115648 A1 | 12/2005 |
| WO | WO 2006/111124 A2 | 10/2006 |
| WO | WO 2006/111124 A3 | 10/2006 |
| WO | WO 2006/118569 | 11/2006 |
| WO | WO 2006/118570 | 11/2006 |
| WO | WO 2007/022122 | 2/2007 |
| WO | WO 2009/148569 | 12/2009 |
| WO | WO 2010/002460 | 1/2010 |
| WO | WO 2010/027455 | 3/2010 |

OTHER PUBLICATIONS

Aminian, K., Coalbed Methane—Fundamental Concepts, Petroleum & Natural Gas Engineering Department, West Virginia University.

Barik, et al., Biological Production of Ethanol from Coal Synthesis Gas, University of Arkansas, Fayetville Arkansas pp. 131-154.

Bumpus, J., Regulation of Coal Polymer Degradation by Fungi (DE-FG22-94PC94209), Nov. 30, 1998.

Catcheside, et al., Biological processing of coal, Appl Microbiol Biotechnol (1999) 53: 16-24, © Springer-Verlag.

Demain, et al., Cellulase, Clostridia, and Ethanol, Microbiology and Molecular Biology Reviews Mar. 2005 p. 124-154.

Gray, I., Reservoir Engineering in Coal Seams: Part 1—The Physical Process of Gas Storage and Movement in Coal Seams, Society of Petroleum Engineers 1986.

Hargreaves, S., Exxon profit soars, but misses forecasts, CNNMoney. com, May 1, 2008.

Isbister et al., Chapter 7, Biogasification of Low Rank Coal, Microbial Transformations of Low Rank Coals pp. 139-156, © 1993 by CRC Press, Inc.

Jain, et al., Anaerobic bioprocessing of Wyodak (USA) coal, FUEL 1991, vol. 70 May p. 573-576.

Kalscheuer, et al., Microdiesel: *Escherichia coli* engineered for fuel production, Microbiology (2006) 152, p. 2529-2536.

Kim et al., Composition of corn dry-grind ethanol by-prodcuts: DDGS, wet cake, and thin stillage, Bioresource Technology 99 (2008) 5165-5176.

Klasson, et al., Direct Bacterial Conversion of Coal to Liquid Fuels, Microbial Transformations of Low Rank Coal Chapter 5, p. 93-110. Crawford, D.L. (Ed.) Microbial Transformations of Low Rank Coal, CRC Press, Boca Raton 223 p.

Larsen, et al., Solvent Extraction of Coals during Analytical Solvent Swelling, A Potential Source of Error, Energy & Fuels 1991, 5, 57-59, © 1991 American Chemical Society.

Percival et al., Toward an Aggregated Understanding of Enzymatic Hydrolysis of Cellulose: Noncomplexed Cellulase Systems, Biotechnology and Bioengineering, vol. 88, No. 7, Dec. 30, 2004.

Scott, A., Improving Coal Gas Recovery with Microbially Enhanced Coalbed Methane, Coalbed Methane: Scientific Environmental and Economic Evaluation, Mastaletze, M., Glikson, M., and Golding, S. Editors 1999.

Scott, A., Limitations and Benefits of Microbially Enhanced Coalbed Methane, INTERGAS '95, May 15-19, 1995, the University of Alabama, Tuscaloosa, Alabama p. 423-431.

Shaw et al., The Role of Initial Reaction Conditions in Direct Coal Liquefaction, Ind. Eng. Chem. Res. 1989, 28, 1795-1801.

Shui, et al., Effect of hydrothermal treatment on the extraction of coal in the $CS_2$/NMP mixed solvent, Fuel 85 (2006) p. 1798-1802.

Toerien, et al., Anaerobic Digestion, 1. The Microbiology of Anaerobic Digestion, Water Research, vol. 3, pp. 385-416, Pergamon Press (1969).

Yoshii et al., Unusual effects of catechol upon the hydroliquefaction of coal, Letters to the Editor, FUEL 1982 vol. 61, Sep. 1982, p. 865-866.

Walsh, J.B., Effect of pore pressure and confining pressure on fracture permeability, International Journal of Rock Mechanics and Mining Sciences & Geomechanics Abstracts vol. 18, Issue 5, Oct. 1981, pp. 429-435.

Zhu, et al., Dissolution of cellulose with ionic liquids and its application: a mini-review, Green Chemistry, 2006, 8, 325-327.

Coalbed Methane, Wikipedia p. 1-6.

Darcy, Wikipedia p. 1-2.

Methanogenesis, Wikipedia p. 1-3.

Phosphorus Acid, Wikipedia p. 1-4.

International Search Report and Written Opinion for PCT/US 09/03917, mailed Aug. 13, 2009.

International Search Report and Written Opinion for PCT/US 09/04572, mailed Oct. 5, 2009.

International Search Report and Written Opinion for PCT/US 09/04945, mailed Oct. 22, 2009.

Declaration of Non-Establishment of International Search Report and Written Opinion for PCT/US 09/058144, mailed Jan. 20, 2010.

International Search Report and Written Opinion for PCT/US 10/03131, mailed Feb. 8, 2011.

International Search Report and Written Opinion for PCT/US 10/03133, mailed Feb. 10, 2011.

International Search Report and Written Opinion for PCT/US 09/03341, mailed Jul. 23, 2009.

\* cited by examiner

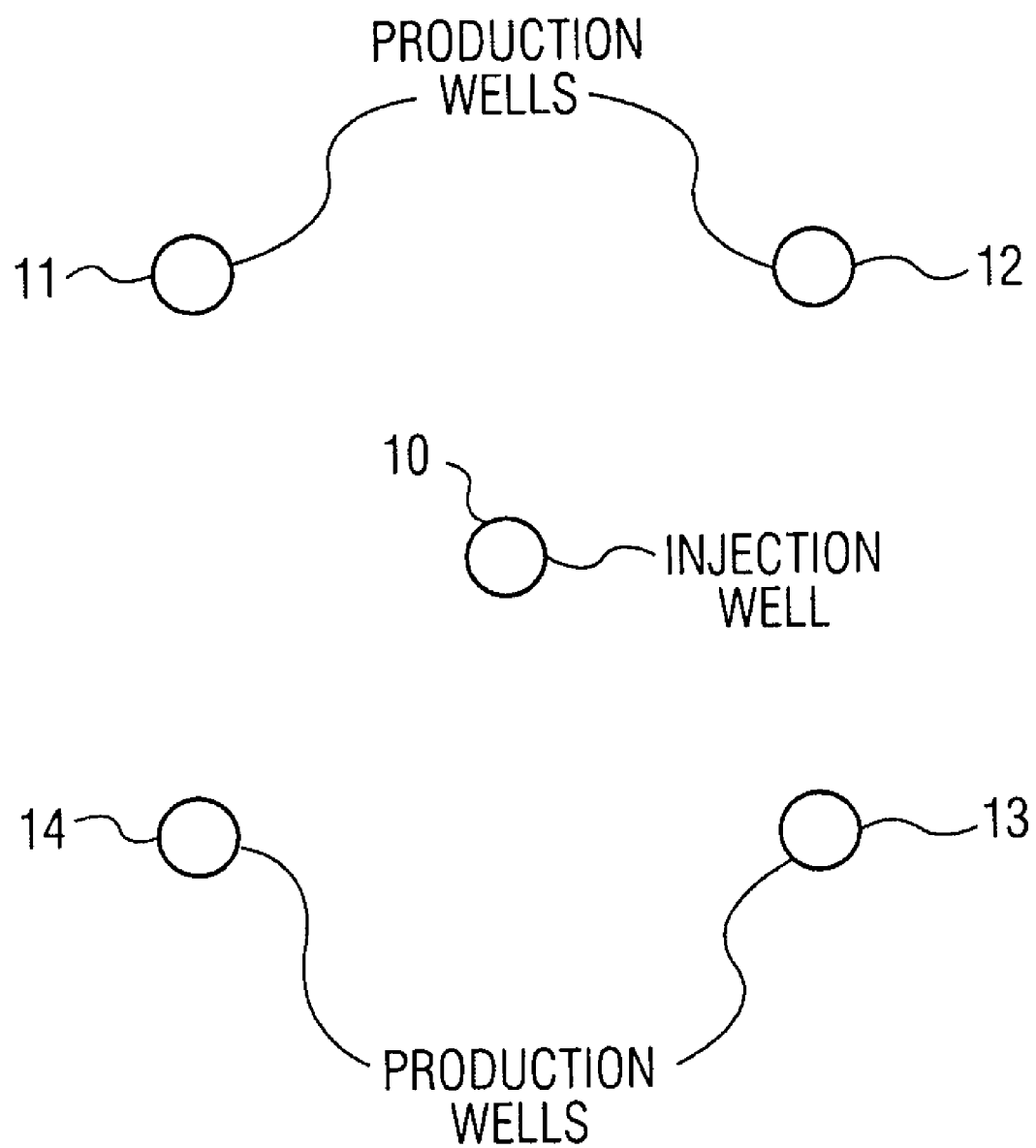

METHOD FOR OPTIMIZING IN-SITU BIOCONVERSION OF CARBON-BEARING FORMATIONS

This application claims the priority of U.S. Provisional Application Ser. No. 61/133,757, filed Jul. 2, 2008, the disclosures of which are hereby incorporated by reference in their entireties.

The present invention relates to the production of methane, carbon dioxide, gaseous and liquid hydrocarbons, and other valuable products from subterranean carbon bearing formations, in-situ. In a preferred embodiment, such production utilizes indigenous and/or non-indigenous microbial consortia that are capable of converting a carbon bearing material such as shale or coal to a desired product.

Methanogenesis (also known as biomethanation) is the production of methane by microbes. The production of methane is an important and widespread form of microbial metabolism; and methanogenesis in microbes is a form of anaerobic respiration.

Generally, the hereinbelow-described methods of treating subterranean formations are intended to increase the susceptibility of large carbonaceous molecules therein, such as comprise coal, to bioconversion into methane and other useful hydrocarbon products by indigenous and/or non-indigenous microbial consortia that are effective for such bioconversion; for example, microbial consortia that comprise methanogens and other bacteria for producing methane from coal. Such microbial consortia for producing methane are referred to as "methanogenic" and the methanogens within such consortia are the microbes that convert hydrogen to methane.

Bacterial consortia for bioconversion and nutrients therefore are generally known in the art and such consortia and nutrients, as well as others may be used in the present invention for bioconversion of carbonaceous deposits.

In general, the present invention relates to a process for treating subterranean formations to increase the susceptibility of large carbonaceous molecules therein, such as comprise shale or coal (as is found in subterranean formations), to bioconversion. Such subterranean deposits or formations are sometimes referred to as "coal seams or deposits" in the case of coal, or "shale deposits" in the case of shale. In a preferred embodiment, such conversion employs indigenous and/or non-indigenous microbial consortia.

For example, U.S. Pat. No. 6,543,535 and U.S. Published Application 2006/0254765 disclose representative microorganisms and nutrients, and the teachings thereof are incorporated by reference.

In a bioconversion process in accordance with an embodiment of the invention, fluid is injected into the coal or shale deposit in order to introduce various materials into the deposit that are useful for the bioconversion of coal or shale to various products. In a preferred embodiment such product comprises methane. The fluid is injected into the deposit through one or more injection wells and flows through the deposit to one or more production wells where the injected fluid is withdrawn from the deposit along with product produced by the bioconversion. In accordance with an aspect of the present invention, the permeability of the bed is increased by reducing net stress in at least a portion of the bed thereby to increase fluid flow through the bed, which increases the flow of materials introduced with the injected fluid and the flow of products produced in the bioconversion. In accordance with another aspect of the invention, by controlling pressures at the injection well and at the production wells, the flow of materials introduced with the injection fluid may be controlled to provide for a desired distribution of such materials through the deposit to thereby facilitate bioconversion of coal or shale therein to desired product.

In one embodiment, the present invention relates to a process for increasing the permeability of such subterranean formations thereby expanding the influence of such microbial consortia (and resources complimentary thereto) so as to thereby increase the susceptibility of those large carbonaceous molecules to bioconversion by such microbial consortia.

The permeability increasing process of the present invention comprises injecting fluid (preferably a liquid such as water) into the deposit by way of at least one injection well and removing product and injected fluid from the deposit by use of at least one production well, and controlling the pressure by use of the injected fluid to such an extent that the fluid pressure within at least a portion of the deposit is increased to a pressure greater than the fluid pressure within that portion of the deposit prior to injection of such fluid. In a preferred embodiment, the liquid (preferably water) includes one or more materials useful in obtaining the desired product from the deposit. For example, such materials may include nutrients for the bioconversion and/or microbes useful in the bioconversion.

In accordance with an aspect of the invention, the fluid pressure is increased to reduce the effective stress on the deposit. The effective stress tends to close the cleats and to reduce permeability within the deposit. Insofar as the vertical pressure on a deposit does not change, changes in fluid pressure in the deposit result in changes in effective stress. The permeability is related particularly to the effective normal stress across the cleats because these appear to conduct most fluids. Increasing fluid pressure within the deposit decreases net stress and increases permeability.

The invention will be further described with respect to a coal deposit and the production of a product comprising methane, but such teachings are also applicable to other solid carbonaceous deposits such as shale and to the production products other or in addition to methane by bioconversion. For example, microbial consortia are known in the art for producing, for example, cetane and/or butane and the present invention is also applicable to producing such products and others by bioconversion of subterranean carbonaceous deposits such as shale or coal. In such a process, indigenous and/or added microbial consorta may be used in such a bioconversion. Appropriate nutrients for the applicable microbial consortia may be added with the injected fluid. More particularly, a coal seam normally includes fluid and in particular water. The fluid pressure in the coal seam is dependent upon the depth thereof, with such fluid pressure (psi) normally being equal to the depth multiplied by 0.433 psi per foot of depth. In accordance with an embodiment of the present invention in which coal is bioconverted to methane, a fluid is pumped into the coal seam through one or more injection wells and the injected fluid, as well as conversion product is removed through one or more production wells, with the bioconversion process being operated such that the injected fluid increases the fluid pressure in at least a portion of the coal seam to a pressure greater than the normal fluid pressure in that portion of the coal seam (the normal fluid pressure being the fluid pressure at the depth of such portion in the absence of the injected fluid).

In accordance with an embodiment of the invention, permeability in the coal deposit is increased by decreasing the net stress on at least a portion of the coal deposit that is being treated. The net stress on the portion of the coal seam is decreased by increasing the fluid pressure within such portion of the coal seam. The change in net stress is approximated by the following:

$$\Delta\sigma = s(p_0 - p)$$

where:
- $p_0$=original fluid pressure in the applicable portion(s) of the coal seam, psia
- p=new fluid pressure in the applicable portion(s) of the coal seam, psia
- s=a constant that equals 0.572

The effective stress prior to changing fluid pressure in the coal seam can be approximated at any given depth D by:

$$\sigma = 0.572D$$

Thus by purposefully increasing the fluid pressure within the subterranean coal formation to above its initial condition, and maintaining that fluid pressure during the treatment, the flow of fluids, including nutrients in the injected fluid, any microbes in the injected fluid and generated methane, carbon dioxide, and hydrocarbons may be optimized.

The change in permeability based on a change in net stress may be approximated as follows:

$$k = k_0 \left[ \exp\left(\frac{-0.003\Delta\sigma}{(k_0)^{0.1}}\right) + 0.0002(\Delta\sigma)^{1/3}(k_0)^{1/3} \right]$$

where:
- $k_0$=original permeability at original net stress, millidarcies
- k=permeability at the new net stress, millidarcies
- $\Delta\sigma$=the difference between original net stress and new net stress, psia In one embodiment, the process is operated to increase permeability by at least 5%. In another embodiment, permeability is increased by at least 15%.

The maximum fluid pressure at which the process may be reasonably operated may be limited by that point at which the fluid pressure in the subterranean formation exceeds its tensile strength, causing large fractures to form and propagate in the formation, in either a vertical or horizontal plane. These pressure-induced fractures may form large fluid channels through which the injected fluids, nutrients, microbial consortia and generated methane may flow, thereby decreasing the ability to effectively treat the coal deposit. In particular, the forming of large fractures will cause fluid to flow through large channels formed by the fractures which reduces effective distribution of material throughout the deposit. Thus, the process is operated in a manner to increase fluid pressure within the seam to obtain a desired permeability without exceeding the tensile strength of the coal deposit that will produce such large fractures.

Operation of the process in subterranean formations at a fluid pressure above initial or hydrostatic conditions and at optimum net effective stress will increase inter-well permeability as the process proceeds, and the efficiency of the process.

In one embodiment, during at least a portion of the bioconversion process, the fluid pressure within at least a portion of the coal seam is increased by controlling the pressure of the injected fluid within the coal seam such that the fluid pressure therein (as compared to the fluid pressure in such portion in the absence of injected fluid) is increased by at least 5%. In another embodiment, such fluid pressure is increased by at least 10%. In a further embodiment, the fluid pressure is increased by at least 15%. As hereinabove indicated, the pressure increase is preferably not to a value such that large fractures are produced in the coal in that such fractures result in the formation of large channels that reduce the ability to achieve an effective distribution of injected fluid throughout the coal seam.

In one embodiment, the coal seam permeability increasing process of the present invention comprises injecting fluid into the coal seam by way of at least one injection well and controlling the pressure of such introduction to such an extent that the fluid pressure within at least a portion of the coal seam exceeds the normal fluid pressure in that portion of the coal seam.

In one embodiment, the coal seam permeability increasing process of the present invention comprises controlling release of fluid from at least one production well to control the fluid pressure within the coal seam to such an extent that the fluid pressure within at least a portion of the coal seam exceeds the normal fluid pressure in that portion of the coal seam.

In one embodiment, the coal seam permeability increasing process of the present invention comprises injecting fluid into the coal seam by way of at least one injection well and releasing fluid from the coal seam by way of at least one production well, and controlling the fluid pressure within at least a portion of the coal seam to increase the fluid pressure in that portion of the coal seam by controlling the pressure of introduction of the fluid into at least one injection well and controlling release of fluid from at least one production well.

As would be appreciated by a person of ordinary skill in the art, the pressures at injection wells and production wells can be controlled by pumping, capping, increasing input, decreasing output, decreasing input, increasing output, and similar methods known in the art. As would be further appreciated by a person of ordinary skill in the art, the aforementioned methods either alone or in combination, could be used to increase fluid pressure within at least a portion of the coal seam to exceed the normal fluid pressure in that portion of the coal seam.

By such pressure manipulations the hereinabove-described and hereinbelow-described coal seam permeability increasing process of the present invention may also be utilized to control distribution of fluid flow, and hence the direction and deposit of amendments containing microbial consortia and/or nutrient resources supportive thereof, and like entities useful to the methanogenic processes.

In one preferred embodiment, the number of production wells exceeds the number of injection wells, and the difference in fluid pressure between the fluid introduced at an injection well and the pressure at which injected fluid and product is withdrawn at each of the production wells is employed to control the distribution of flow between the injection well and the respective production wells. In this manner, distribution of materials that are introduced into the coal seam by use of the injection fluid can be controlled to promote effective distribution of such materials throughout the coal seam. Since the injected fluid distribution between the multiple production wells and the injection well for such production wells is controlled by pressure difference, such distribution may be controlled while simultaneously increasing fluid pressure within at least a portion of the coal seam to reduce effective stress and increase permeability.

The manner in which injected fluid distribution may be controlled between production wells and an injection well may be illustrated with reference to the drawing.

As shown in the drawing, there is an injection well 10 and four production wells 11, 12, 13 and 14. Assuming that when operating the production wells 11, 12, 13 and 14 at the same pressure, there is an unequal distribution of fluid being withdrawn from the respective wells 11, 12, 13 and 14, whereby there is an unequal distribution of injected fluid into the production areas of the coal bed, the fluid pressure at one or more of the respective wells 11, 12, 13 and 14 may be adjusted to increase and/or decrease the pressure difference between the injection well and the applicable production well to increase and decrease, respectively, flow of injected fluid to the applicable production well. In this manner, the distribution of injected fluid into the coal bed in various portions of the coal bed may be controlled.

In preferred embodiments, the fluid pressure within a portion of the coal seam is a pressure high enough to reduce net stress without providing large fractures in the coal. It will be appreciated by those of ordinary skill in the art that lower rank coal is more compressible than higher rank coal, such that a pressure useful for overcoming net effective stress in one coal seam may be a pressure that would cause fracture in another coal seam.

As used herein, coal refers to any of the series of carbonaceous fuels ranging from lignite to anthracite. The members of the series differ from each other in the relative amounts of moisture, volatile matter, and fixed carbon they contain. The lowest in carbon content, lignite or brown coal, is followed in ascending order by subbituminous coal or black lignite (a slightly higher grade than lignite), bituminous coal, semibituminous (a high-grade bituminous coal), semianthracite (a low-grade anthracite), and anthracite.

The coal may be lignite or any form or rank of coal, ranging from brown coal to anthracite.

The amount of bioconversion products produced by methanogenesis in the coal seam, and the rate of such production, is a function of several factors, including but not necessarily limited to, the specific microbial consortia present, the nature or type of the coal seam, the temperature and pressure of the coal seam, the presence and geochemistry of the water within the coal seam, the availability of nutrients required by the microbial consortia to survive and grow, and the presence or saturation of methane and other bioconversion products. In accordance with an embodiment of the invention, by increasing and preferably optimizing the permeability of the coal seam by increasing fluid pressure within at least a portion of the coal seam during the process for producing methane, bioconversion of the coal to methane, carbon dioxide, and other hydrocarbons can be optimized by increasing one or more of: the delivery and dispersal of nutrients into the coal seam; the delivery and dispersal of microbial consortia in the coal seam; the amount of surface area of the coal seam that is exposed to the microbial consortia; the removal and recovery of the generated methane, carbon dioxide, and other hydrocarbons from the coal seam.

The rate of carbon bioconversion is proportionate to the amount of surface area available to the microbes, to the population of the microbes, and to the movement of nutrients into the system and the movement of bioconversion products from the system. The amount of surface area available to the microbes is proportionate to the percentage of void space, or porosity, of the subterranean formation; and the ability of gases and liquids to flow through the subterranean formation is in turn dependent on its porosity. All subterranean formations are to some extent compressible. Thus, in accordance with the invention, by reducing the net effective stress upon a coal seam by increasing the fluid pressure therein, one can improve the coal seam's permeability, porosity, internal surface area available for bioconversion, and the ability to move nutrients, microbes and generated methane, carbon dioxide, and other hydrocarbons into and out of the coal seam.

Numerous modifications and variations of the present invention are possible in light of the teachings herein and, therefore, within the scope of the claims, the invention may be practiced other than as described herein with reference to particular embodiments thereof.

What is claimed is:

1. A process for bioconverting a carbon-bearing subterranean formation, and thereby producing a product comprising at least one hydrocarbon, said process for bioconverting comprising: injecting fluid into a carbon-bearing deposit, located in said subterranean formation, by way of at least one injection well, removing injected fluid and product from said carbon-bearing deposit through at least one production well, said bioconverting being effected by a microbial consortia capable of bioconverting said carbon-bearing deposit so as to produce at least one hydrocarbon, and controlling fluid pressure within at least a portion of said carbon-bearing deposit by use of said injected fluid, said fluid pressure being controlled such that the fluid pressure within at least a portion of said carbon-bearing deposit exceeds the fluid pressure that normally exists in that portion, but does not exceed the tensile strength of said carbon-bearing deposit, thereby avoiding the inducing and/or propagating of fractures in said carbon-bearing deposit.

2. The process of claim 1, wherein said carbon-bearing deposit is selected from the group consisting of: coal seams, coal deposits, shale deposits, and combinations of the foregoing.

3. The process of claim 2, wherein said carbon-bearing deposit is a coal seam and wherein said bioconverting of said carbon-bearing subterranean formation further comprises increasing the permeability of said coal seam by reducing the net stress in at least a portion of said coal seam, wherein said net stress in said portion of said coal seam is decreased by increasing the fluid pressure within said portion of said coal seam, and wherein the change in permeability based on the change in net stress is approximated as follows:

$$k = k_0 \left[ \exp\left( \frac{-0.003 \Delta \sigma}{(k_0)^{0.1}} \right) + 0.0002 (\Delta \sigma)^{1/3} (k_0)^{1/3} \right]$$

where:
$k_0$=original permeability at original net stress, millidarcies
$k$=permeability at the new net stress, millidarcies
$\Delta \sigma$=the difference between original net stress and new net stress, psia; and
wherein the change in said net stress is approximated by the following:

$$\Delta \sigma = s(p_0 - p)$$

where:
$p_0$=original fluid pressure in the applicable portion(s) of the coal seam, psia
$p$=new fluid pressure in the applicable portion(s) of the coal seam, psia
$s$=a constant that equals 0.572.

4. The process of claim 3, wherein said fluid pressure within at least a portion of said coal seam exceeds the fluid pressure that normally exists in that portion by at least 5%.

5. The process of claim 3, wherein said fluid pressure within at least a portion of said coal seam exceeds the fluid pressure that normally exists in that portion by at least 10%.

6. The process of claim 3, wherein said fluid pressure within at least a portion of said coal seam exceeds the fluid pressure that normally exists in that portion by at least 15%.

7. The process of claim 3, wherein said permeability is increased by at least 5%.

8. The process of claim 3, wherein said permeability is increased by at least 15%.

9. The process of claim 1, wherein said injected fluid contains water.

10. The process of claim 1, wherein the hydrocarbon component of said product comprising at least one hydrocarbon is selected from the group consisting of methane, cetane, butane, and combinations of the foregoing.

11. The process of claim 1, wherein the hydrocarbon component of said product comprising at least one hydrocarbon is in gaseous form.

12. The process of claim 1, wherein the hydrocarbon component of said product comprising at least one hydrocarbon is in liquid form.

13. The process of claim 1, wherein said injected fluid contains a microbial consortia that is capable of bioconverting a carbon-bearing material to said product.

14. The process of claim 13, wherein said microbial consortia is selected from the group consisting of: microbial consortia that are present in said carbon-bearing subterranean formation, microbial consortia that are added to said carbon-bearing subterranean formation, and combinations of the foregoing.

15. The process of claim 1, wherein said injected fluid contains nutrients or other resources complimentary to microbial consortia.

16. The process of claim 1, wherein said injected fluid contains microbial consortia that are capable of bioconverting a carbon-bearing material to said product and wherein said injected fluid also contains nutrients or other resources complimentary to microbial consortia.

17. The process of claim 1, wherein said bioconverting of said carbon-bearing subterranean formation further comprises achieving a desired distribution through said carbon-bearing deposit of materials introduced with the injection fluid by controlling pressure at said at least one injection well.

18. The process of claim 17, wherein the method of controlling the pressure at said at least one injection well is selected from the group consisting of: pumping, capping, increasing input, decreasing output, decreasing input, increasing output, and combinations of the foregoing.

19. The process of claim 1, wherein said bioconverting of said carbon-bearing subterranean formation further comprises achieving a desired distribution through said carbon-bearing deposit of materials introduced with the injection fluid by controlling pressure at said at least one production well.

20. The process of claim 19, wherein the method of controlling the pressure at said at least one production well is selected from the group consisting of: pumping, capping, increasing input, decreasing output, decreasing input, increasing output, and combinations of the foregoing.

21. The process of claim 1, wherein said bioconverting of said carbon-bearing subterranean formation further comprises achieving a desired distribution through said carbon-bearing deposit of materials introduced with the injection fluid by controlling pressure at said at least one injection well and by controlling pressure at said at least one production well.

22. The process of claim 21, wherein the method of controlling both the pressure at said at least one injection well and the pressure at said at least one production well are independently selected from the group consisting of: pumping, capping, increasing input, decreasing output, decreasing input, increasing output, and combinations of the foregoing.

23. The process of claim 1, wherein said bioconverting of said carbon-bearing subterranean formation further comprises increasing the permeability of said carbon-bearing deposit by reducing net stress in at least a portion of said carbon-bearing deposit thereby increasing fluid flow through said carbon-bearing deposit to increase the flow of materials introduced with the injected fluid and the flow of products produced in the bioconversion.

24. The process of claim 23, wherein said fluid flow through said carbon-bearing deposit is optimized so as to maximize the production of said product.

25. The process of claim 24, wherein said at least one product is methane.

26. The process of claim 23, wherein said permeability is increased by at least 5%.

27. The process of claim 23, wherein said permeability is increased by at least 15%.

* * * * *